United States Patent
Lu et al.

(10) Patent No.: US 12,138,011 B2
(45) Date of Patent: Nov. 12, 2024

(54) IMAGE REGISTRATION METHOD AND SYSTEM THEREOF

(71) Applicant: Apollo Medical Optics, Ltd., Taipei (TW)

(72) Inventors: Chih Wei Lu, Taipei (TW); Sung Wei Lu, Taipei (TW); Jia-Wei Lin, Taipei (TW); I-Ling Chen, Taipei (TW); Tuan Shu Ho, Taipei (TW)

(73) Assignee: Apollo Medical Optics, Ltd., Taipei (TW)

( * ) Notice: Subject to any disclaimer, the term of this patent is extended or adjusted under 35 U.S.C. 154(b) by 131 days.

(21) Appl. No.: 17/607,853

(22) PCT Filed: Apr. 30, 2020

(86) PCT No.: PCT/US2020/030877
§ 371 (c)(1),
(2) Date: Oct. 29, 2021

(87) PCT Pub. No.: WO2020/223572
PCT Pub. Date: Nov. 5, 2020

(65) Prior Publication Data
US 2022/0211273 A1    Jul. 7, 2022

Related U.S. Application Data

(60) Provisional application No. 62/841,197, filed on Apr. 30, 2019.

(51) Int. Cl.
*A61B 5/00* (2006.01)
*G06T 7/33* (2017.01)
*G16H 30/40* (2018.01)

(52) U.S. Cl.
CPC .............. *A61B 5/0035* (2013.01); *G06T 7/33* (2017.01); *G16H 30/40* (2018.01);
(Continued)

(58) Field of Classification Search
CPC ... A61B 5/0035; A61B 5/0068; A61B 5/0071; A61B 5/0075; A61B 5/0066;
(Continued)

(56) References Cited

U.S. PATENT DOCUMENTS 6,032,071 A     2/2000  Binder
10,142,549 B2 * 11/2018 Wang ..................... H04N 23/69
(Continued)

FOREIGN PATENT DOCUMENTS

WO    WO 2018/005316 A1    1/2018

OTHER PUBLICATIONS

Christos Nikolaos E et al, (Image registration of follow-up examinations in digital dermoscopy, IEEE, pp. 1-4, 2013) (Year: 2013).*

*Primary Examiner* — Amara Abdi
(74) *Attorney, Agent, or Firm* — Chang-Hsing Liang

(57) ABSTRACT

Provided herein are image registration methods comprising providing a wide view image of a target area by a first imager; providing a narrow view image of the target area by a second imager; aligning the narrow view image on the wide view image of the target area; capturing an optical image by an optical imager, wherein the optical imager is configured to locate the optical image in the narrow view image; and displaying the position of the optical image on the narrow view image and the wide view image of the target area; and the systems thereof.

16 Claims, 10 Drawing Sheets

(52) U.S. Cl.
CPC ............... *G06T 2207/10056* (2013.01); *G06T 2207/10072* (2013.01); *G06T 2207/30004* (2013.01)

(58) Field of Classification Search
CPC . A61B 5/444; G06T 7/33; G06T 2207/10056; G06T 2207/10072; G06T 2207/30004; G06T 2207/10101; G06T 2207/30088; G16H 30/40
See application file for complete search history.

(56) References Cited

U.S. PATENT DOCUMENTS

| | | | |
|---|---|---|---|
| 2013/0070961 A1* | 3/2013 | Kia | G06T 7/33 382/103 |
| 2013/0089235 A1* | 4/2013 | Yoon | G06V 20/10 382/153 |
| 2014/0210949 A1* | 7/2014 | Berkovich | G06T 17/05 348/46 |
| 2015/0294490 A1 | 10/2015 | Lin et al. | |
| 2016/0166194 A1* | 6/2016 | Gareau | A61B 5/14552 600/328 |
| 2017/0169596 A1* | 6/2017 | Yonezawa | G06T 5/50 |
| 2018/0360375 A1* | 12/2018 | Holmes | G06T 7/0012 |
| 2019/0332875 A1* | 10/2019 | Vallespi-Gonzalez | G06V 20/584 |

\* cited by examiner

IMAGE REGISTRATION METHOD AND SYSTEM THEREOF

BACKGROUND OF THE INVENTION

According to the statistic of World Health Organization, skin cancer has grown year-on-year in the past decade globally, closely related to lifestyle, aging society, and the destruction of the global ozone layer.

Clinically, the diagnosis of any particular skin condition including skin cancer is made by gathering pertinent information regarding the presenting skin lesion(s), including the location (such as arms, head, legs), symptoms (pruritus, pain), duration (acute or chronic), arrangement (solitary, generalized, annular, linear), morphology (macules, papules, vesicles), and color (red, blue, brown, black, white, yellow). An optical diagnosis system may be used in accessing the skin conditions besides the routine skin biopsy.

SUMMARY OF THE INVENTION

The present invention provides an image registration method to precisely position and track a target area during a medical diagnosis process. The present invention further provides an image registration system having two imagers sharing the same optical element to achieve precisely optical image registration.

The present invention relates to an image registration method, which comprises providing a wide view image of a target area by a first imager; providing a narrow view image of the target area by a second imager; aligning the narrow view image on the wide view image of the target area; capturing an optical image by an optical imager, wherein the optical imager is configured to locate the optical image in the narrow view image; and displaying the position of the optical image on the narrow view image and the wide view image of the target area.

The present invention also relates to an image registration system, which comprises a first imager configured to capture a wide view image of a target area; and an optical module comprising a second imager and an optical imager, the second imager and the optical imager sharing the same objective, wherein the optical imager is configured to capture an optical image, and the second imager is configured to capture a narrow view image of the target area to align the narrow view image on the wide view image of the target area and display the position of the optical image on the narrow view image and the wide view of the target area.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which.

DETAILED DESCRIPTION OF THE INVENTION

Image registration is the process of transforming different sets of data into one coordinate system. Data may be multiple photographs, data from different sensors, times, depths, or viewpoints. Registration is necessary in order to be able to compare or integrate the data obtained from these different measurements. For example, one of the main purposes of the image registration is to accurately locate the target areas to employ a high-resolution noninvasive optical scan during the diagnosis and treatment process. It can be used to repeatedly find the target area of interests in subsequent examinations, therefore achieving continuous tracking and following-up medical services.

In general, optical images, such as optical coherence tomography (OCT) and reflectance confocal microscopy (RCM) images, having high resolution and small field of view (FOV) are not easy to accurately find a target part/area of interests, and often time the same part/area cannot be found later among the large area, thus impossible to track the target part/area of interest; such difficulty leads to increases of the diagnosis time and cost of treatments. For example, for the resolutions of ~1 μm, the field of view is about hundred micrometers that would cause difficult positioning the scanning area in a target area (e.g., a lesion on the skin).

Based on the above-mentioned image alignment issues, it is necessary to develop a precise image alignment/registration system, and more specifically a skin image alignment/registration system, making it easier to position and track the target area of the skin for diagnoses and treatments. This invention can help to aim the scanning area precisely in the lesion, and to record the scanned points to confirm the full lesion being examined. Therefore, the efficiency of whole examining process can be much improved, and physician can go back to scan the same spot while following up the patient after the last examination.

In some embodiments provide an image registration method especially suitable for skin diagnosis to precisely position the location of a target area during a skin navigation. The present invention also provides an image registration system having at least two imagers sharing the same optical element to accurately achieve the optical image positioning.

Figure 1:
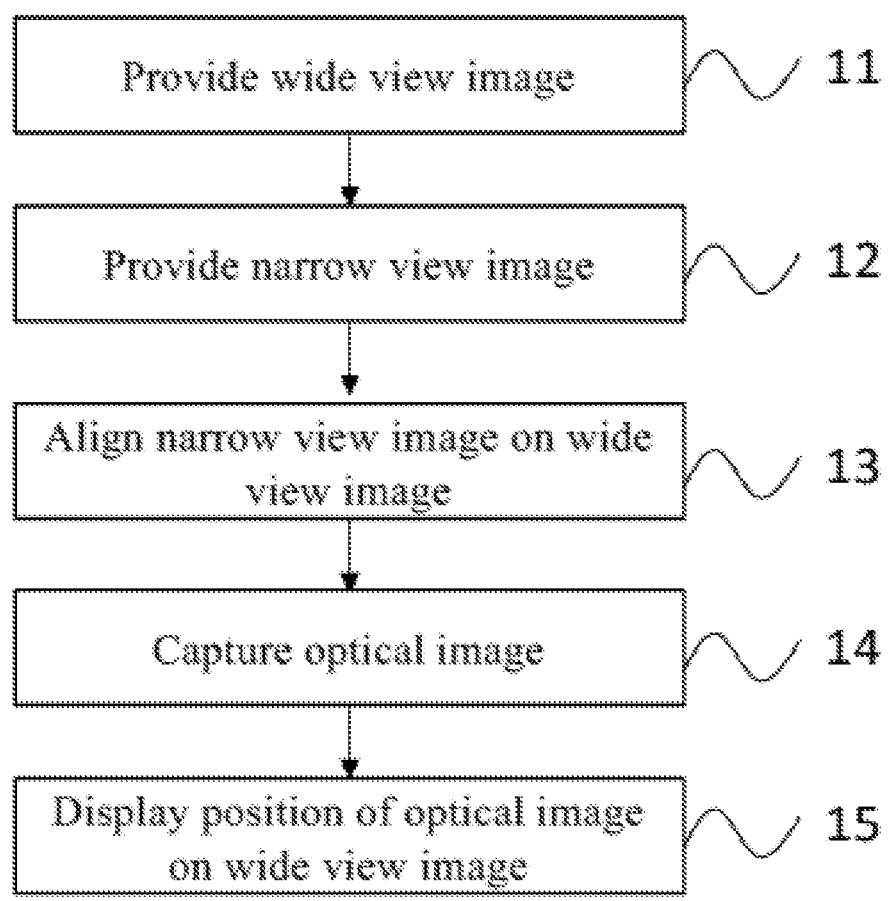
FIG. 1 illustrates an exemplary flowchart of a general method of invention image registration.

FIG. 1 shows an exemplary flowchart of a general method of invention image registration, which comprises the following steps of providing a wide view image of a target area by a first imager (step 11); providing a narrow view image of the target area by a second imager (step 12); aligning the narrow view image on the wide view image of the target area (step 13); and capturing an optical image by an optical imager (step 14), wherein the optical imager is configured to locate the optical image in the narrow view image; and displaying the position of the optical image on the wide view image (step 15) to achieve registering the optical image on narrow view image and the wide view image of the target area.

In some embodiments, the optical image is an optical coherence tomography (OCT) image, a reflectance confocal microscopy (RCM) image, a two-photon luminescence microscopy (TPL) image, a second harmonic generation microscopy (SHG) image, a third harmonic generation microscopy (THG) image, a fluorescence confocal microscopy (FCM) image, or the like. In some embodiments, the optical imager is the corresponding device/system that can produce an optical coherence tomography (OCT) image, a reflectance confocal microscopy (RCM) image, a two-photon luminescence microscopy (TPL) image, a second harmonic generation microscopy (SHG) image, a third harmonic generation microscopy (THG) image, a fluorescence confocal microscopy (FCM) image, or the like. In certain embodiments, the optical image is an OCT image, or a RCM image.

To achieve the feature extracting and matching processes during the image registration, there are two ways for realizing these two processes, one is area based matching technique, another is feature based matching technique. For skin image registration, feature based matching technique is preferred to be selected for image extraction and matching process due to the similar and difficult to distinguish features of adjacent skin colors.

Additionally, there are also the issues of skin deformation, image rotating and scale difference between image frames during a skin scanning process. For these considerations, feature based matching technique will be a suitable way for skin image registration. In the feature-based technique, it also can be divided into two ways, a blobs-based technique and a corner-based technique. As for the skin image having the property of high magnification with less sharp corner or clear edge, a blob-based technique will be a preferred way for skin image feature extracting and matching. In some embodiments, a blob-based technique is at least one selected form a group consisting of SURF algorithm, SIFT algorithm, and KAZE algorithm, preferably SURF algorithm and SIFT algorithm, however, it is not limited thereto. In some embodiment, SURF algorithm is a preferred one owing to less sensitive of skin deformation, skin image rotation and scale difference between frames. Additionally, it also has better performance in image registration processing speed to achieve real time skin image navigation.

Figure 2:
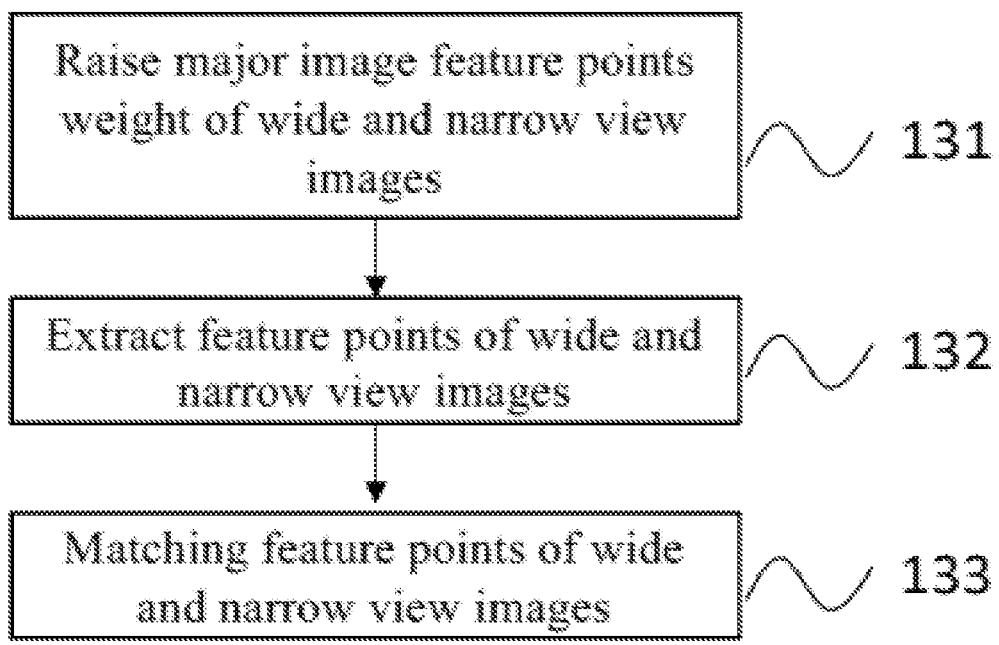
FIG. 2 illustrates an example of image aligning processing.

In order to precisely register the optical image on the wide view image, in some embodiment, as shown in FIG. 2, the processing of aligning narrow view image on the wide view image comprises a step of raising major image feature points weighting of the wide view image and the narrow view image (step 131); a step 132 of extracting the feature points of the wide view image and the narrow view image; and a step 133 of matching the feature points of the wide view image and the narrow view image.

In some embodiments, the step of raising major image feature points weighting comprises downsizing and/or image blurring of the wide view image and narrow view image. Referring to the downsizing process, the ratio is preferably 30 to 90%, more preferably 50 to 80%, more preferably 60 to 70%, but not limited thereto. The downsizing step can effectively boost the speed of image registration process and make the resolution of the wide view image substantially equal/close to the resolution of the narrow view image. In some embodiments, it also has the function of enhance the feature weighting of major image point and reduce the feature weighting of minor image point.

In other embodiments, the image blurring process mainly shows the effect of raising the major image feature points weighting and reduce the minor image feature points weighting. Therefore, if the narrow view image and the wide view image both have higher resolution, the step of downsizing and/or image blurring will make a good effort of promoting accuracy and the timeliness of the image registration during an image scanning (e.g. skin image diagnosis).

In some embodiments, the step of extracting feature point comprises at least one property of scale, rotation and affine substantially invariance. In certain embodiment, the property satisfies the invariance of scale, rotation and affine. In the step of extracting feature point, the substantially invariance refers to one of scale, rotation, and affine, not necessarily completely unchanged where if of identifiable features, a minor change of property (at least one of scale, rotation, affine) is allowable.

In some embodiments, the resolution of the wide view image substantially equals or close to the resolution of the narrow view image. The definition of "substantially equals or close to" has a difference around 0 to 25 μm, preferably 0 to 20 μm, preferably 0 to 15 μm, preferably 0 to 10 μm, preferably, 0 to 5 μm, and most preferably 0 to 3 μm. The closer resolutions of narrow view image and wide view image, the closer of the detailed image features of the two images to improve the success rate of image registration.

Figure 3A:
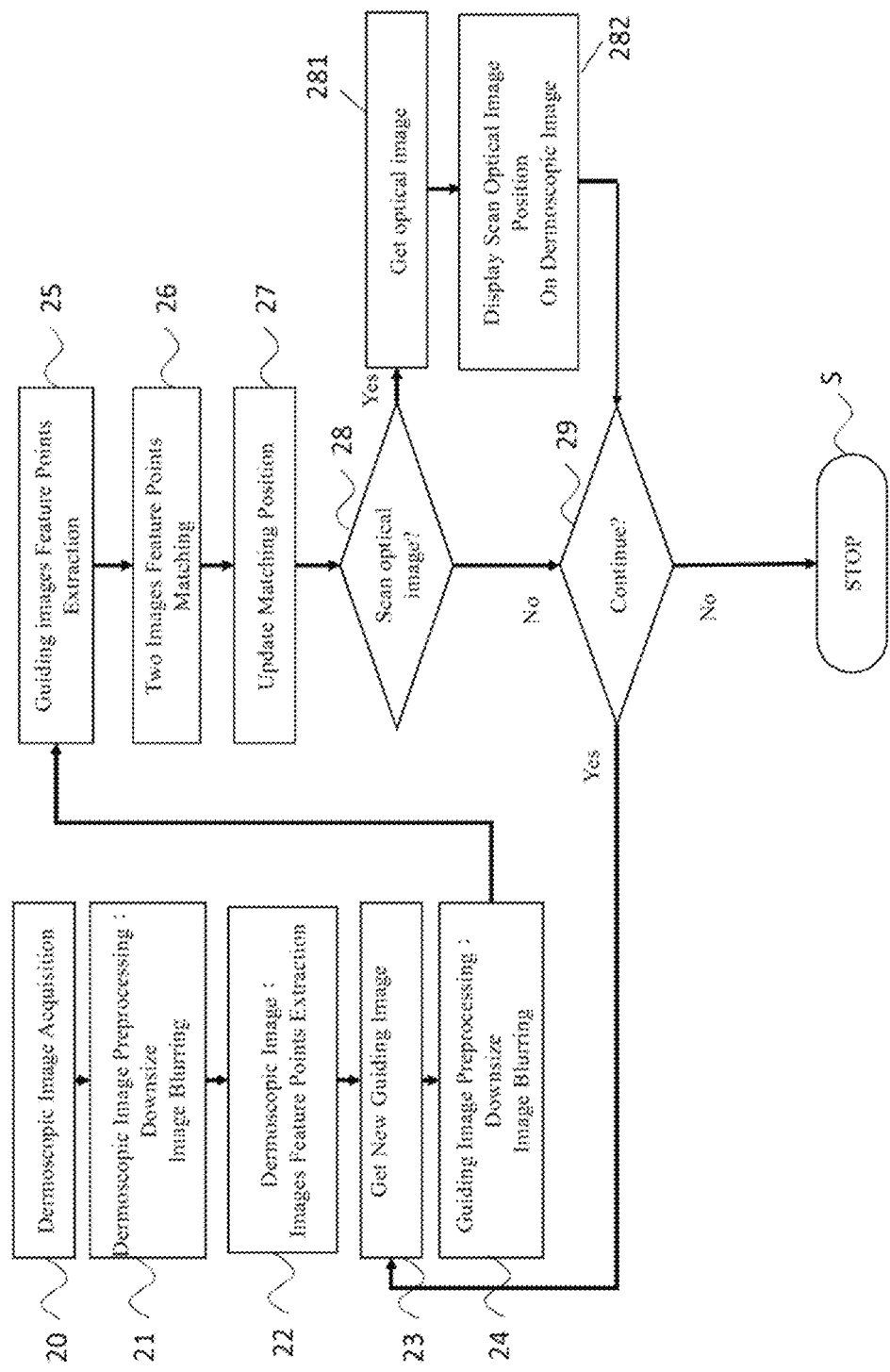
FIG. 3A/B show exemplary flowcharts of image registration processing.

FIG. 3A/B further provide flowcharts illustrating exemplary image registration processing applying to skin optical image registrations (e.g. optical coherence tomography (OCT) image, reflectance confocal microscopy (RCM) image, two-photon luminescence microscopy (TPL) image, second harmonic generation microscopy (SHG) image, third harmonic generation microscopy (THG) image, or fluorescence confocal microscopy (FCM) image, or the like).

In some embodiments, an exemplary skin image registration method, as shown in FIG. 3A, comprises the following steps: step 20: acquiring a wide view image of a dermoscopic image (i.e., a wide view image) through a dermoscopy (i.e., a first imager); step 21: downsizing and image blurring the dermoscopic image (i.e., the wide view image) to raise the major image feature points weighting thereof; step 22: extracting image feature points of the dermoscopic image; step 23: gating a narrow view image of a new guiding image through an image guiding imager (i.e., a second imager); step 24: downsizing and image blurring the guiding image (i.e., a narrow view image) to raise the major image feature points weighting thereof; step 25: extracting feature points of guiding image (i.e., a narrow view image); step 26: matching the two images (dermoscopic image and new guiding image) feature points; step 27: updating the matching position of the dermoscopic image and the guiding image; step 28: decide to scan an optical image (i.e. OCT, RCM, TPL, SHG, THG, or FCM images); if yes, go to step 281: getting an optical image after the optical image scanning; step 282: displaying the position of the optical image on the dermoscopic image. However, if the image matching is not correct in step 282, a new guiding image should be continuously acquired in step 29 and step 23. When accomplishing the optical image registration, a user will stop continuously acquiring a new guiding image in step S.

In some embodiments, as illustrated in FIG. 3A, there is no need to scan optical image. If so, the processing of image registration does not involve with an optical image, and the image registration process is completed. In some embodiments provide an image registration method comprising providing a wide view image of a target area by a first imager; providing a narrow view image of the target area by a second imager; aligning the narrow view image on the wide view image of the target area; displaying the position of the narrow view image on the wide view image of the target area. The processing of aligning the narrow view image on the wide view image is the same with or without the inclusion of an optical image.

Figure 3B:
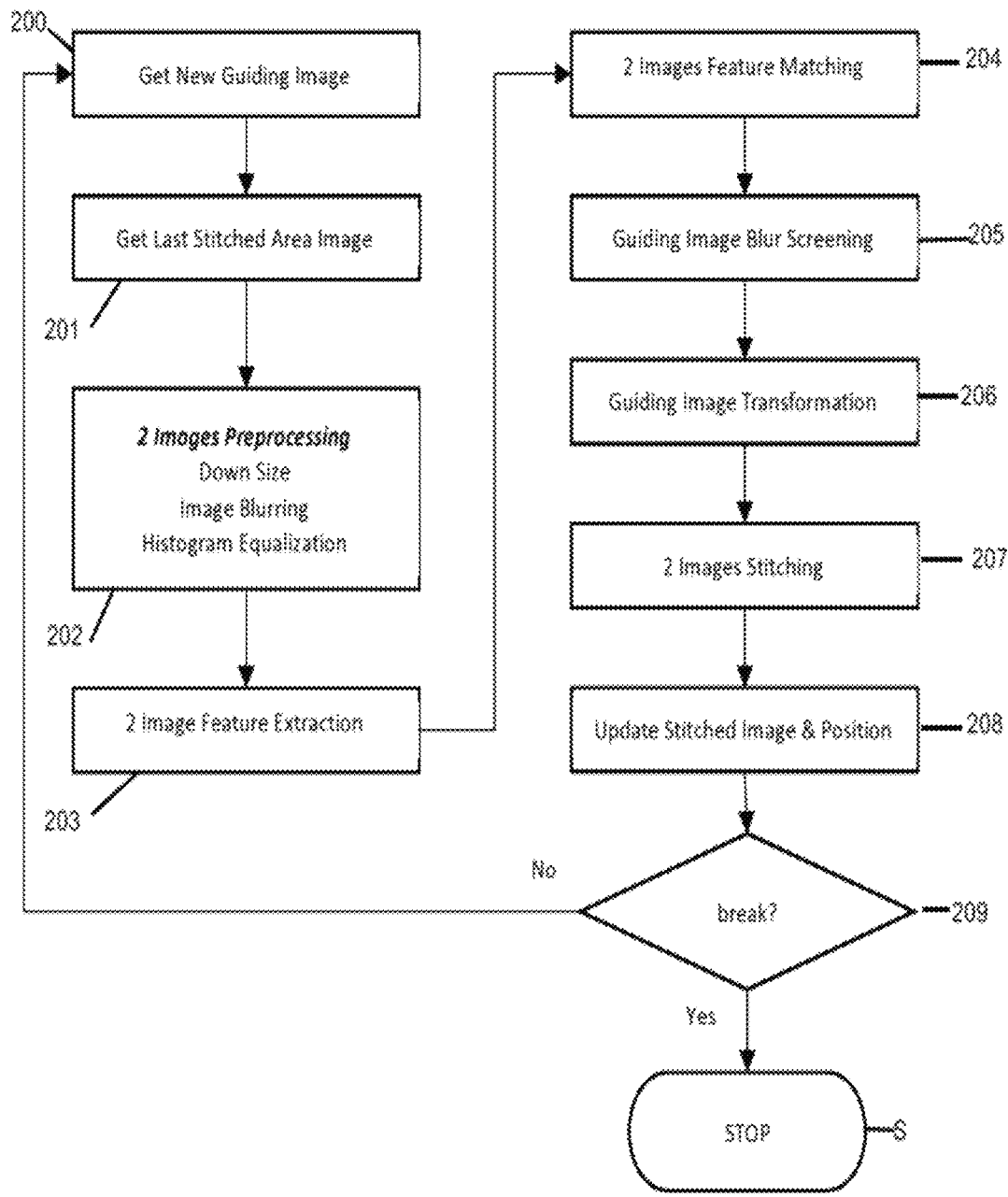

In other embodiments provide invention image registration comprising a step of mosaicking (a guiding image mosaicking). The method involves comparing the overlapping area between frame to frame and stitch these images in real time as illustrated in FIG. 3B. In Step 200: acquiring new guiding image; step 201: getting last stitched area image; step 202 involves 2 images processing comprising downsizing, image blurring, and histogram equalization; step 203: 2 image feature extraction; step 204: 2 images feature matching; step 205: guiding image blur screening; step 206: guiding image transformation; step 207: 2 images stitching; step 208: update stitched image and position; step 209: deciding if a break is needed, if yes, go to step S (stop), if no, go to step 200 to get another new guiding image and start the processing again. In this method, any images can be used to obtain the stitched image with identified position. A step involving histogram equalization is to enhance the image characteristic after removing the minor image features to improve the matching reliability. In some embodiments provide an image mosaicking method comprising acquiring a new guiding image; getting a last stitched area image; processing said guiding image and said last stitched area image comprising downsizing, image blurring and histogram equalization; extracting image features; matching features of said guiding image and said last stitched area image; blur screening said guiding image; transforming said guiding image; and stitching the guiding image with the last stitched area image and updating said resulted stitched image and position.

Figure 4A:
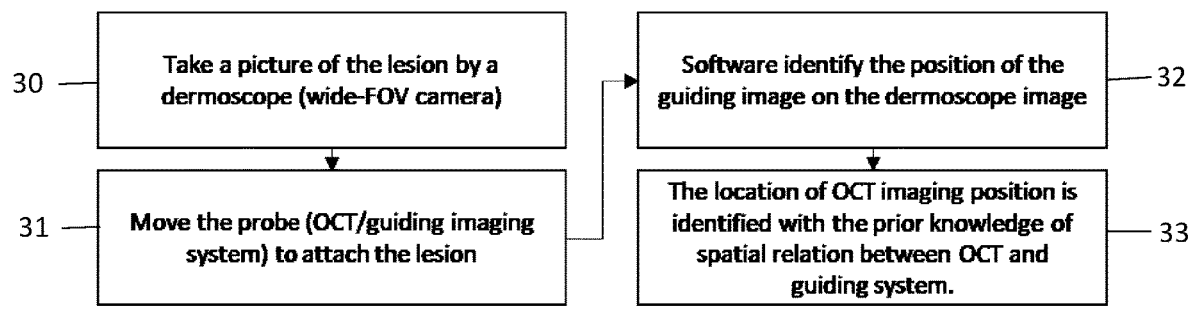
FIG. 4A-D illustrate exemplary invention image registration methods under various embodiments.

In some embodiments the invention method applies to image registration of an OCT image. Since the field of view of the dermoscope image (a wide view image) is much wider than the guiding image (a narrow view image), the area could cover most general lesion size. As illustrated in FIG. 4A, in Step 30: the lesion image with the dermoscope (a wide view image) is retrieved by attaching the probe (may comprise a narrow view imager and an optical view imager) on the lesion. Next, in step 31, the OCT/guiding system is attached to the lesion and capturing the guiding image continuously. In step 32, a software utilizing invention methods disclosed herein would identify current position on the dermoscope image displayed by image registration process, therefore the system would constitute the image in real time in step 33. Since the spatial relation between OCT image system and the guiding image system (where a narrow view image is taken) is fixed, the OCT imaging location at that instance can also be identified.

Figure 4B:
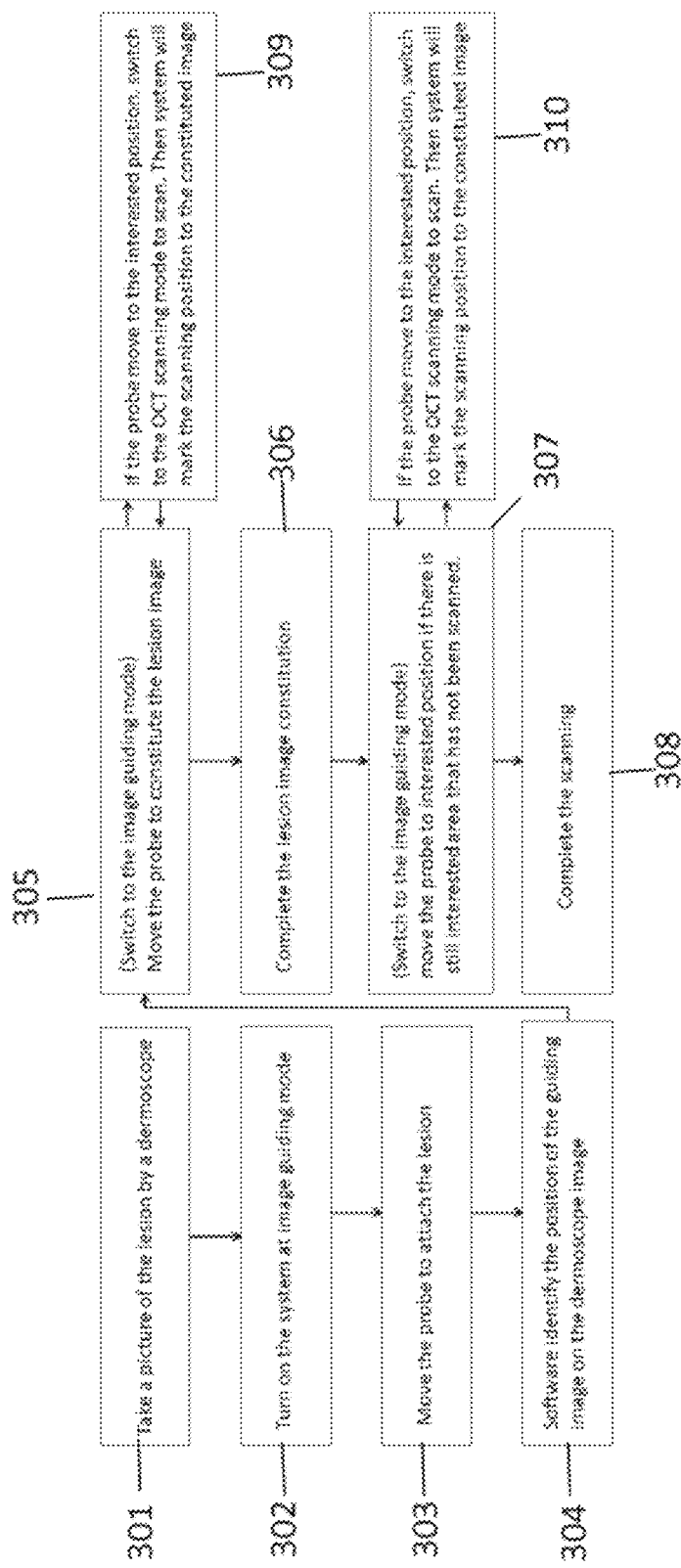

In the case the OCT images (or other imaging modality that provide information beneath the superficial surface) and the guiding images cannot be acquired synchronously (for example, at the situation where the OCT and guiding system cannot be separated optically and may interfere each other), the present invention provides yet another embodiment of the image registration method as illustrated in FIG. 4B. The problem of this scenario is the OCT imaging location is marked based on the last guiding image acquired before the OCT scanning begins and may not be accurate if the user is moving the probe during the switching process and/or OCT scanning. In step 301, an image of the lesion is taken by a wide view imager, e.g., a dermoscope. Step 302: turn on the system at image guiding mode. Step 303: move the probe to attach the lesion. Step 304: the position of the narrow view image (e.g., the guiding image) is identified by a software. Step 305: after switching to the image guiding mode in the system, move the probe to constitute the target image (e.g., lesion image). Here, if the probe moves to the interested position, Step 309 provides switching to the OCT canning mode to scan (i.e., acquiring an optical image by an optical imager). Then system will mark the scanning position to the constituted image. Step 306: complete the lesion image constitution. Step 307: move the probe to interested position if there is still interested area that has not been scanned. Step 310 provides that if the probe moves to the interested position, switching to the OCT scanning mode to scan (i.e., acquiring the optical image by an optical imager). Then the system will mark the scanning position to the constituted image (i.e., the optical image).

Figure 4C:
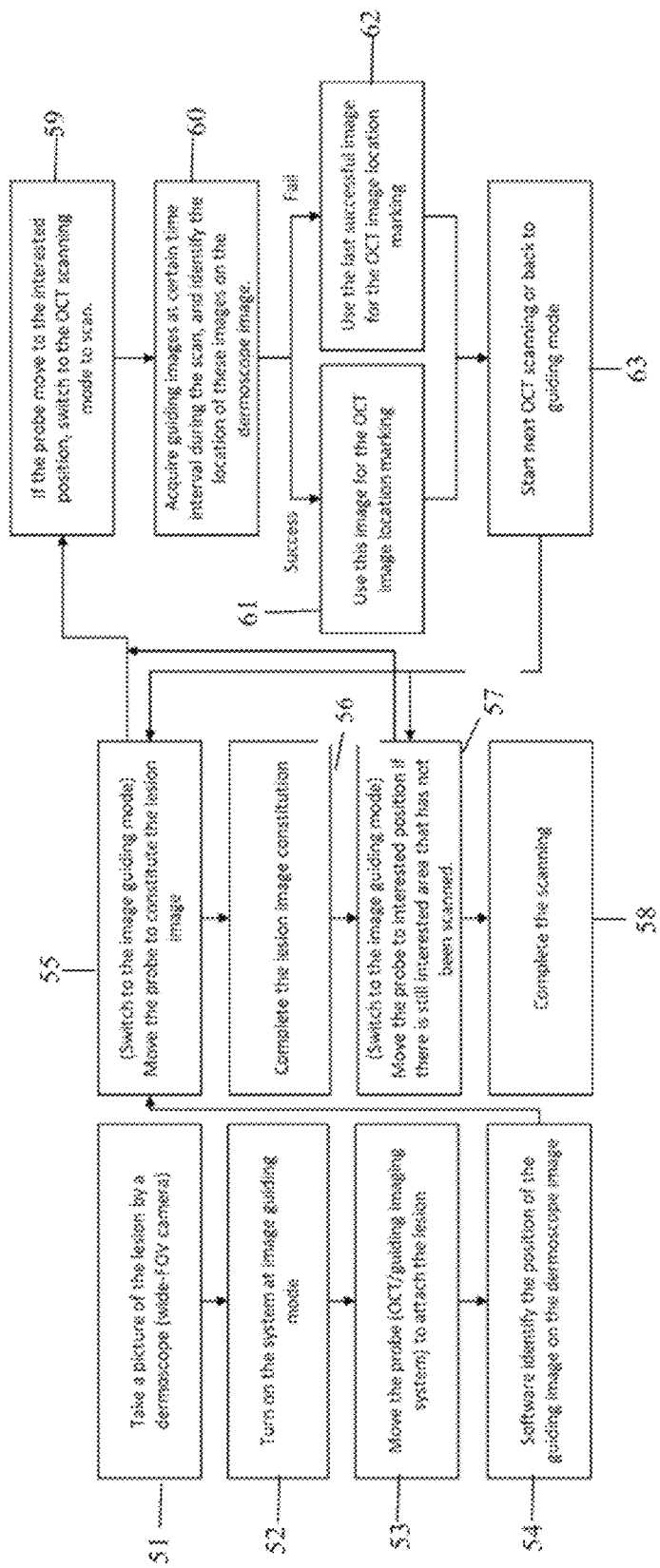

In certain embodiments, such as in the OCT B-scan mode, the guiding image (i.e., the narrow view image) cannot be acquired synchronously, but the OCT scanning location can be registered with the OCT images (i.e., the optical images) themselves with mosaicking, the present invention provides yet another embodiment of the image registration method as illustrated in FIG. 4C. In step 51, an image of the lesion is taken by a wide view imager, e.g., a dermoscope. Step 52: turn on the system at image guiding mode. Step 53: move the probe to attach the lesion. Step 54: the position of the narrow view image (e.g., the guiding image) is identified by a software utilizing the invention methods disclosed herein. Step 55: after switching to the image guiding mode in the system, move the probe to constitute the target image (e.g., lesion image). If the probe moves to the interested position, in step 59, switching to the OCT scanning mode to scan. Then, step 60 may be taken to acquire guiding images (i.e., the narrow view images) at certain time interval during the scan and identify the location of these images on the dermoscope image. If failing to identify the location, step 62 is taken to use the last successful image for the OCT image location marking. If successful, Step 61 is taken to use the image for the OCT image location marking. After step 63, starting next OCT scanning or going back to guiding mode at Step 55 or Step 57. Step 56 completes the lesion image constitution. If there is still an interested area that has not been scanned, in Step 57, moves the probe to the interested position. Step 58 completes the entire scanning.

Figure 4D:
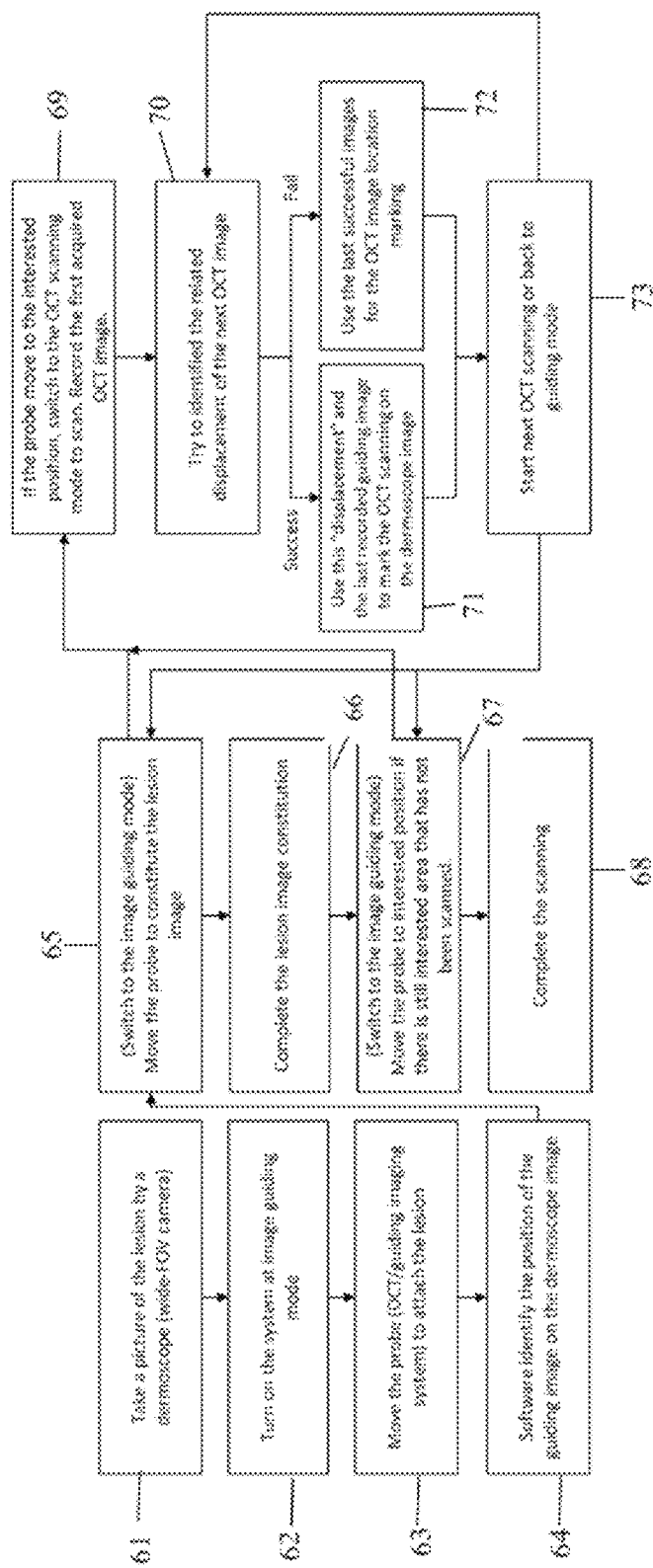

In certain embodiments, such as in the OCT E-scan mode, the OCT and guiding image cannot be acquired synchronously, but the OCT scanning location can be registered with the OCT images themselves with mosaicking, the present invention provides yet another embodiment of the image registration method as illustrated in FIG. 4D. In step 61, an image of the lesion is taken by a wide view imager, e.g., a dermoscope. Step 62: turn on the system at image guiding mode. Step 63: move the probe to attach the lesion. Step 64: the position of the narrow view image (e.g., the guiding image) is identified by a software utilizing the invention methods disclosed herein. Step 65: after switching to the image guiding mode in the system, move the probe to constitute the target image (e.g., lesion image). If the probe moves to the interested position, in step 69, switching to the OCT scanning mode to scan and record the first acquired OCT image (i.e., an optical image). Then, step 70 may be taken to try to identify the related displacement of the next OCT image. If failing to identify, step 72 is taken to use the last successful image for the OCT image location marking. If successful, Step 71 is taken to use the displacement and the last recorded guiding image to mark the OCT scanning on the dermoscope image. After this, in step 73, starting next OCT scanning or going back to guiding mode at Step 65 or Step 70. Step 66 completes the lesion image constitution. If there is still an interested area that has not been scanned, in Step 67, moves the probe to the interested position. Step 68 completes the entire scanning.

Figure 5:
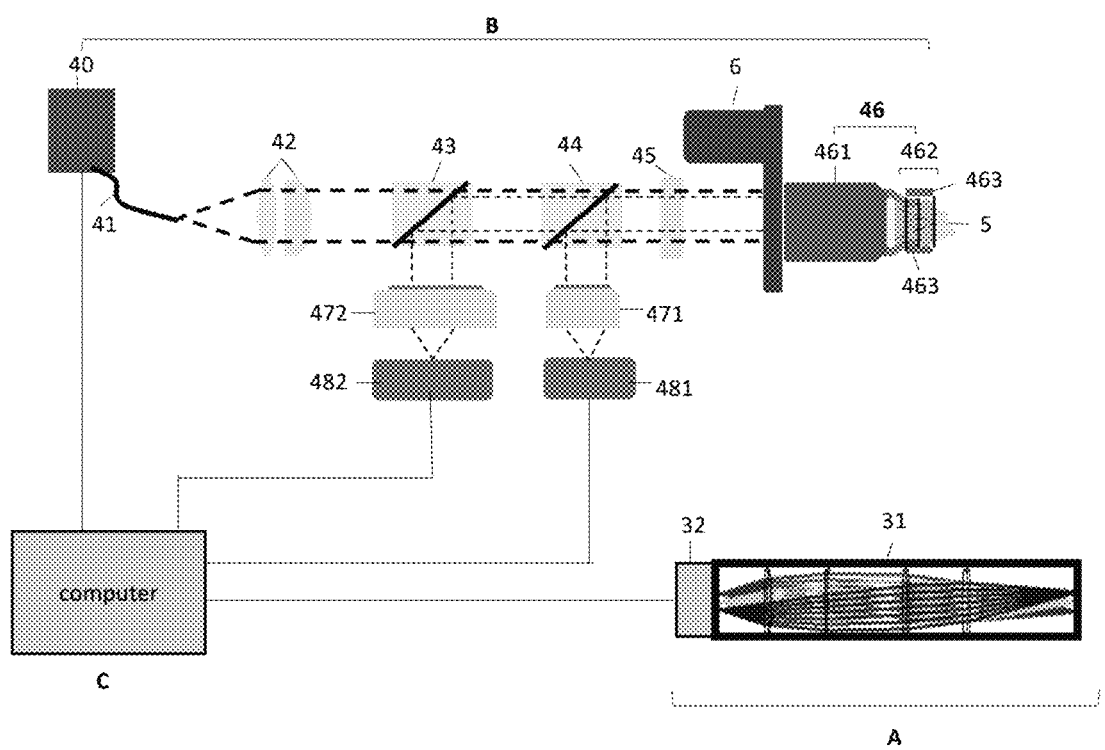
FIG. 5 illustrates an example of the image registration system.

FIG. 5 provides an exemplary invention image registration system. A first imager A (e.g., a dermoscope) is configured to capture a wide view image of a target area. An optical module B comprises a second imager and an optical imager, wherein a computer C is configured to connect and control the first imager A and the optical module B. The second imager and the optical imager sharing the same objective 46 to make the FOV of the optical image overlap with the FOV of the narrow view image provided by the second imager. The optical imager is configured to capture an optical image, and the second imager is used to capture a narrow view image of a target area, in which the narrow view image will be aligned to the wide view image of the target area and the optical image will be displayed on the narrow view image and wide view image of the target area.

Detailly, as illustrated in FIG. 5, the first imager A capturing a wide view image is at least, for example, one dermoscopy, epiluminescence microscopy and an image mosaicking module. A skilled person in the art would readily recognize and adapt to use other suitable first imager. In some embodiments, the first imager A comprises a first imager optical lenses 31 and a first camera 32, which could be controlled via a computer C. In addition, in some embodiments, the light source of the dermoscopy and/or the epiluminescence microscopy comprises at least one LED and/or Wood's lamp, but not limited thereto. Other suitable light source in accordance with the practice of this invention can be readily recognized by a skilled person in the art. An optical module B comprises two imagers including the second imager and the optical imager, wherein the second imager provides a narrow view of image guiding mode and the optical imager provides an optical image. The optical image is preferably an optical coherence tomography (OCT) image, a reflectance confocal microscopy (RCM) image, a two-photon luminescence microscopy (TPL) image, a second harmonic generation microscopy (SHG) image, a third harmonic generation microscopy (THG) image, a fluorescence confocal microscopy (FCM) image, or combinations thereof. More preferably, the optical image is an OCT image or a RCM image. With regard to the second imager, it comprises a light source 463 surrounded the objective module 46 to provide a light on a target area of a sample 5; and a beam splitter 44 used to direct the light signal to a second camera 481 via a projection lens 471. In addition, with regard to the optical imager, it comprises a light source 40 to provide a light into an optical lens 42 through an optical fiber 41; the light passing through a polarization beam splitter 43, beam splitter 44, and quarter wave plate 45 to convert the light with circular polarization; an objective module 46 having an objective 461 and an interference means 462 to pass the light on the sample 5. When the light backscattered from the sample 5, the polarization beam splitter 43 directs the light to the third camera 482 through a projection lens 472. Computer C is configured to control the light source 40 and process images from the second and third camera 481 and 482.

The alignment system of the present invention can continuously align optical images on the dermoscopic images and present a plurality of scanning positions of the optical images on the dermoscopic images in order to clearly indicate/label the scanning positions of the optical images.

Figure 6:
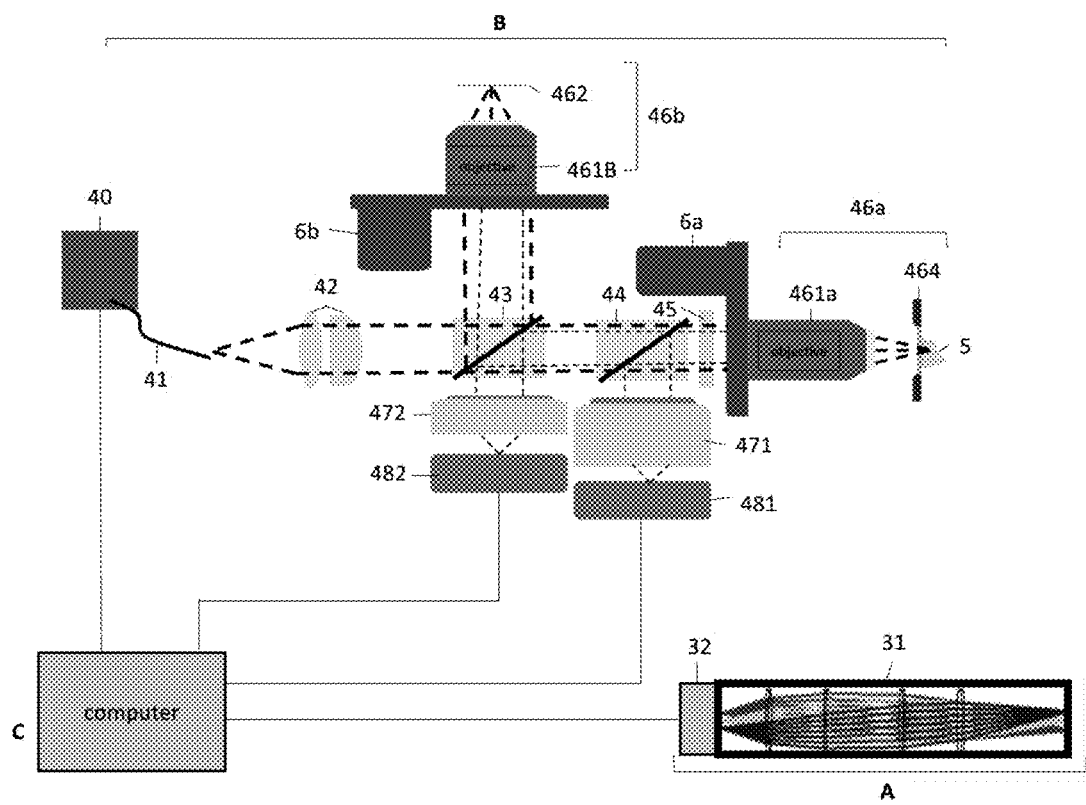
FIG. 6 illustrates yet another embodiment of an image registration system.

FIG. 5 demonstrates an exemplary optical system comprising a Mirau type interferometer; on the other hand, FIG. 6 illustrates a Linnik type interferometer. Other suitable optical imagers as disclosed herein can be readily adopted by a skilled person in the art. For example, a person skilled in the art can chose Michelson type interferometer or Mach-Zehnder interferometer in necessary. Besides, a person skilled in the art can also replace other optical system, such as RCM, TPL, SHG, THG, or FCM, to meet the requirement in necessary.

The only difference between FIG. 6 and FIG. 5 is the objective 46a and 46b, wherein the objective 46a provides sample arm from the sample 5 covered by the glass plate 463, and the objective 46b provides reference arm from the mirror 462.

In the present invention, the optical image is well registered on the dermoscopic image owning to the optical imager and the image guiding imager share the same optical objective, and the FOV of the optical imager is substantially overlap or the same with the FOV of the image guiding imager.

In some embodiments provide image registration systems comprising: a first imager configured to capture a wide view image of a target area; and an optical module comprising a second imager and an optical imager, the second imager and the optical imager sharing the same objective, wherein the optical imager is configured to capture an optical image, and the second imager is configured to capture a narrow view image of the target area to align the narrow view image on the wide view image of the target area and display the position of the optical image on the narrow view image and the wide view of the target area. In certain embodiments, the first imager comprises at least one dermoscope, epiluminescence microscopy and an image mosaicking module. In certain embodiments, the light source of the dermoscope and/or the epiluminescence microscopy comprises at least one LED and/or Wood's lamp. In certain embodiments, the field of view of the first imager is in a range of 5*5 mm to 20*20 mm. In certain embodiments, the field of view of the second imager is in a range of 1*1 mm to 5*5 mm. In certain embodiments, the field of view of the optical imager is in a range of 50*50 µm to 1000*1000 µm. In certain embodiments, wherein the resolution of the wide view image substantially equals to the resolution of the narrow view image. In certain embodiments, the resolution of the wide view image has a difference from the narrow view image around 0 to 25 µm, 0 to 20 µm, 0 to 15 µm, 0 to 10 µm, 0 to 5 µm, or 0 to 3 µm. In certain embodiments, the optical imager is an optical coherence tomography (OCT) device, a reflectance confocal microscopy (RCM) device, a two-photon luminescence microscopy (TPL) device, a second harmonic generation microscopy (SHG) device, a third harmonic generation microscopy (THG) device, a fluorescence confocal microscopy (FCM) device, or combinations thereof.

In some embodiments, the first imager has a field of view (FOV) in a range of 5*5 mm to 20*20 mm, preferably 6*6 mm to 17*17 mm, preferably 10*10 mm to 15*15 mm, but it is not limited thereto. The FOV of the second imager is in a range of 1*1 mm to 5*5 mm, preferably 2*2 mm to 4.5*4.5 mm, preferably 3*3 mm to 4*4 mm, but it is not limited thereto. Besides, the FOV of the optical imager is in a range of 50*50 µm$^2$ to 1000*1000 µm$^2$, preferably 100*100 µm$^2$ to 800*800 µm$^2$, preferably 300*300 µm$^2$ to 600*600 µm$^2$, and preferably 400*400 µm$^2$ to 500*500 µm$^2$, but it is not limited thereto. Because the FOV of the narrow view image overlaps to the FOV of the optical imager, the position of the optical image in the narrow view image are always easy to be tracked, or a marker will be provided to precisely label the position of the optical imager on the narrow view imager.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. An image registration method comprising:
   providing a wide view image of a target area by a first imager wherein the first imager has a field of view (FOV) in a range of 10*10 mm to 15*15 mm;
   providing a narrow view image of the target area by a second imager wherein the second imager has a field of view (FOV) in a range of 1*1 mm to 5*5 mm;
   aligning the narrow view image on the wide view image of the target area;
   capturing an optical image by an optical imager, wherein the optical imager is configured to locate the optical image in the narrow view image to confirm a full lesion being examined, and has a field of view (FOV) in a range of 300*300 $\mu m^2$ to 600*600 $\mu m^2$; and
   displaying position of the optical image on the narrow view image and the wide view image of the target area.

2. The image registration method of claim 1, wherein the step of aligning the narrow view image on the wide view image comprises:
   raising major image feature points weighting of the wide view image and the narrow view image;
   extracting the feature points of the wide view image and the narrow view image with at least one property of scale, rotation and affine invariance; and
   matching the feature points of the wide view image and the narrow view image.

3. The image registration method of claim 2, wherein the step of raising major image points weighting comprises downsizing and/or image blurring of the wide view image and narrow view image.

4. The image registration method of claim 3, wherein the downsize ratio is in a range of 30~90%, 50~80%, or 60~70%.

5. The image registration method of claim 1, wherein the resolution of the wide view image substantially close to the resolution of the narrow view image.

6. The image registration method of claim 2, wherein the step of extracting feature point comprises at least one property of scale, rotation and affine substantially invariance.

7. The image registration method of claim 5, wherein the resolution of the wide view image has a difference from the narrow view image around 0 to 25 µm, 0 to 20 µm, 0 to 15 µm, 0 to 10 µm, 0 to 5 µm, or 0 to 3 µm.

8. The image registration method of claim 1, wherein the first imager comprises at least one dermoscope, epiluminescence microscopy and an image mosaicking module.

9. The image registration method of claim 8, wherein the light source of the dermoscope and/or the epiluminescence microscopy comprises at least one LED and/or Wood's lamp.

10. The image registration method of claim 1, wherein the optical imager is an optical coherence tomography (OCT) device, a reflectance confocal microscopy (RCM) device, a two-photon luminescence microscopy (TPL) device, a second harmonic generation microscopy (SHG) device, a third harmonic generation microscopy (THG) device, a fluorescence confocal microscopy (FCM) device, or combinations thereof.

11. An image registration system comprising:
   a first imager configured to capture a wide view image of a target area wherein the first imager has a field of view (FOV) in a range of 10*10 mm to 15*15 mm; and
   an optical module comprising a second imager and an optical imager wherein the second imager has a field of view (FOV) in a range of 1*1 mm to 5*5 mm and the optical imager has a field of view (FOV) in a range of 300*300 $\mu m^2$ to 600*600 $\mu m^2$,
   the second imager and the optical imager sharing the same objective, wherein the optical imager is configured to capture an optical image and to locate the optical image in the narrow view image to confirm a full lesion being examined; and the second imager is configured to capture a narrow view image of the target area to align the narrow view image on the wide view image of the target area; and
   display position of the optical image on the narrow view image and the wide view of the target area.

12. The image registration system of claim 11, wherein the first imager comprises at least one dermoscope, epiluminescence microscopy and an image mosaicking module.

13. The image registration system of claim 12, wherein the light source of the dermoscope and/or the epiluminescence microscopy comprises at least one LED and/or Wood's lamp.

14. The image registration system of claim 11, wherein the resolution of the wide view image substantially equals to the resolution of the narrow view image.

15. The image registration system of claim 14, wherein the resolution of the wide view image has a difference from the narrow view image around 0 to 25 µm, 0 to 20 µm, 0 to 15 µm, 0 to 10 µm, 0 to 5 µm, or 0 to 3 µm.

16. The image registration system of claim 11, wherein the optical imager is an optical coherence tomography (OCT) device, a reflectance confocal microscopy (RCM) device, a two-photon luminescence microscopy (TPL) device, a second harmonic generation microscopy (SHG) device, a third harmonic generation microscopy (THG) device, a fluorescence confocal microscopy (FCM) device, or combinations thereof.

* * * * *